(12) United States Patent
Auerbach et al.

(10) Patent No.: US 7,316,233 B2
(45) Date of Patent: Jan. 8, 2008

(54) STOCKINETTE EXTREMITY DRAPE

(75) Inventors: David M. Auerbach, Van Nuys, CA (US); Robert Villereal, Gurnee, IL (US); Mylena Holguin, El Paso, TX (US); Rogelio Reyes, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/308,677

(22) Filed: Dec. 3, 2002

(65) Prior Publication Data

US 2004/0103904 A1 Jun. 3, 2004

(51) Int. Cl.
*A61B 19/00* (2006.01)

(52) U.S. Cl. ........................................ 128/849; 128/853

(58) Field of Classification Search ......... 128/849–856
See application file for complete search history.

(56) References Cited

U.S. PATENT DOCUMENTS

| 2,591,783 | A | * | 4/1952 | Craddock | 128/842 |
|---|---|---|---|---|---|
| 3,030,957 | A | * | 4/1962 | Melges | 604/357 |
| 3,968,792 | A | | 7/1976 | Small | 128/132 |
| 3,989,040 | A | | 11/1976 | Lofgren et al. | 128/132 |
| 4,043,328 | A | * | 8/1977 | Cawood | 128/132 D |
| 4,119,093 | A | * | 10/1978 | Goodman | 128/856 |
| 4,153,054 | A | | 5/1979 | Boone | 128/132 |
| 4,253,451 | A | | 3/1981 | Solomon | 128/132 |
| 4,308,864 | A | | 1/1982 | Small et al. | 128/132 |
| 4,397,309 | A | * | 8/1983 | McAllester | 128/855 |
| 4,553,539 | A | | 11/1985 | Morris | 128/132 |
| 4,730,609 | A | * | 3/1988 | McConnell | 128/853 |
| 4,745,915 | A | | 5/1988 | Enright et al. | 128/132 |
| 4,887,615 | A | | 12/1989 | Taylor | 128/850 |
| 5,002,069 | A | * | 3/1991 | Thompson | 128/849 |
| 5,143,091 | A | | 9/1992 | Patnode et al. | 128/853 |
| 5,383,476 | A | | 1/1995 | Peimer et al. | 128/853 |
| 5,433,221 | A | | 7/1995 | Adair | 128/849 |
| 5,494,050 | A | | 2/1996 | Reyes | 128/849 |
| 5,513,655 | A | | 5/1996 | Peimer et al. | 128/853 |
| 5,720,712 | A | | 2/1998 | Joy et al. | 602/3 |
| 5,761,746 | A | | 6/1998 | Brown | 2/243.1 |
| 5,871,014 | A | | 2/1999 | Clay et al. | 128/849 |
| 5,921,242 | A | | 7/1999 | Newman | 128/849 |
| 6,298,855 | B1 | | 10/2001 | Baird | 128/849 |
| 6,382,211 | B1 | | 5/2002 | Crook | 128/849 |

OTHER PUBLICATIONS

Product Brochure, 3M Health Care, 3M Surgical Drapes, Selection Guide.

* cited by examiner

*Primary Examiner*—Michael A. Brown
(74) *Attorney, Agent, or Firm*—Andrew G. Rozycki

(57) ABSTRACT

The invention herein provides an integrated drape for use in surgical procedures involving anatomical extremities and having a unitary assembled structure, said drape comprising: a flexible panel sheet portion having first and second opposing sides and having a fenestration located therethrough; and a flexible elongate sleeve portion having an open proximal end; wherein the open proximal end of said sleeve is integrally attached to the panel sheet and circumscribes the fenestration. The drape readily accommodates various anatomical extremities, permits the creation of a surgical access site at any location for a given extremity, and is presented to the user as a single, one-piece construction reducing or eliminating the need for obtaining and setting up supplemental drapes for a procedure.

18 Claims, 6 Drawing Sheets

STOCKINETTE EXTREMITY DRAPE

FIELD OF THE INVENTION

The invention relates to the field of surgical drapes. In particular, the invention pertains to an improved surgical drape adapted for use in conjunction with medical procedures on anatomical extremities.

BACKGROUND OF THE INVENTION

A variety of surgical drapes have been developed in the medical field for creating a sterile field surrounding the surgery site on the patient. A wide variety of drape configurations, shapes and features have also been developed. For certain anatomical extremities, such as shoulders and knees, for example, a variety of drapes have been designed with structural features which accommodate the geometry of the extremity.

Surgical drapes which are specifically tailored for use with procedures performed on shoulders, knees and arms, are known. Such extremity drapes can include fenestrations through which the limb or extremity is to be inserted to isolate such from the remainder of the body. For example, an extremity drape is described in Enright et al. U.S. Pat. No. 4,745,915, which discloses an open ended tubular cover for an extremity with a sealable "pull-tab" to expose an access opening for surgery. Other drapes have been developed which contain exterior pouches to capture waste tissue and fluids associated with the procedure.

One problem associated with such extremity drapes is the need for additional drapes to fully form the sterile barrier for the patient. Another problem associated with extremity drapes is that they contain features specific for a particular anatomical extremity or surgery location.

There exists a need in the medical field for surgical drapes adapted for use with anatomical extremities while at the same time afford anatomical diversity, e.g., extremity drapes which can be adapted for use with different extremity shapes and sizes without the need for multiple drapes. A further need exists for surgical drapes adapted for use with extremities which are less awkward to assemble and position, and are constructed from fewer materials, relatively compact, and easy to manufacture and use.

SUMMARY OF THE INVENTION

The invention provides an improved surgical drape for use with anatomical extremities. It has been discovered that an extremity drape can be constructed and presented to the user as a simplified, unitary, integrated drape system thus obviating the need for using a plurality of drapes to create a sterile field on the patient. Another advantage of the invention is that a single drape can be adapted for more than one type of extremity, e.g., thigh, foot, arm, or finger, and contains a portion having adjustable length. Yet another advantage of the invention is that it affords the flexibility of various surgical locations within a given extremity. Accordingly, less specificity in manufacturing of the drape is needed.

Furthermore, from a manufacturing standpoint the drape of the invention can be easily re-configured for use with surgical sites associated with extremities, such as the hip or shoulder. Because fewer structural components are used, the integrated extremity drape of the invention can be structured and folded into a relatively compact unit for handling, shipping and storage. Yet another advantage is that more than one drape can readily be used during a procedure, wherein an additional or second drape can be superimposed over a first drape.

The invention provides an integrated drape for use in surgical procedures involving anatomical extremities and having a unitary assembled structure, said drape comprising:
   a) a flexible panel sheet portion having first and second opposing sides and having a fenestration located therethrough;
   b) a flexible elongate sleeve portion having an open proximal end and a closed distal end;

wherein the open proximal end of said sleeve is integrally attached to the panel sheet and circumscribes the fenestration.

In a preferred embodiment, the drape further comprises a reinforcement panel attached to the panel sheet surrounding the fenestration and covering the attachment juncture between the sleeve portion and panel sheet. In a further preferred embodiment, the sleeve portion is composed of fluid impervious material. In one embodiment, the drape further comprises an integrally attached extension panel.

BRIEF DESCRIPTION OF THE DRAWINGS

The invention is further illustrated by the following drawings, none of which are to be construed as limiting the invention to the illustrated embodiments:

FIG. 6A is a side view illustration of a drape portion with the sleeve portion folded with a hand inserted therein according to one embodiment of the invention.

FIG. 6B is a side view illustration of a drape portion and sleeve portion partially extended and an arm inserted therein according to one embodiment of the invention.

FIG. 6C is a side view illustration of a drape portion with the sleeve portion fully extended with an arm therein according to one embodiment of the invention.

FIG. 6D is a side view illustration of a drape portion with the sleeve portion fully extended and arm therein and a created access opening in accordance with one embodiment of the invention.

DETAILED DESCRIPTION OF THE INVENTION

As used herein, the term "integrated" and "integral", and inflections thereof, are meant to indicate that the drape by virtue of contiguous attachment of its portions is presented to the user in single, one-piece construction, and does not require further assembly or attachment of the components at the time of use.

The term "sleeve" is meant to define an elongated partially enclosed configuration having a substantially coextensive hollow interior. The term is meant to encompass a generally tubular configuration, but is not intended to imply limitations as to a particular cross-sectional shape or uniformity of diameter along the length.

Figure 1:
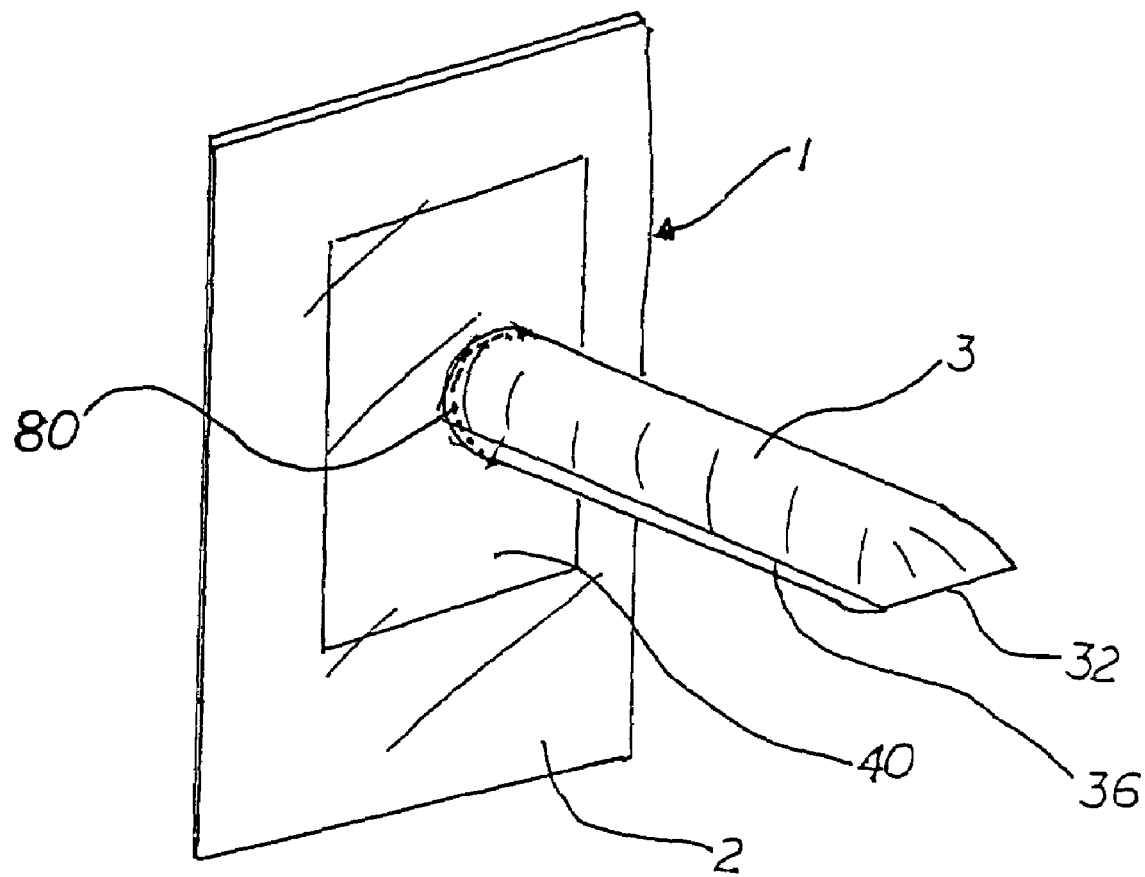
FIG. 1 is an angled side view of a portion of a drape containing the sleeve in accordance with one embodiment of the invention.

Referring to FIG. 1, the integrated drape 1 of the invention is a unitary assembled structure comprising two portions: a panel sheet portion 2 and sleeve portion 3; and is adapted for use in medical and/or medical procedure wherein it is advantageous or beneficial to create a sterile barrier between a surgical site on an extremity and the remainder of the patient's body. The drape of the invention can be used in procedures involving (or anatomy associated with) anatomical extremities including, but not limited to, upper and lower limb arthroscopy, wrist, elbow, hands, feet, ankles, thigh, calve, forearm, and the like. The drape is particularly useful in surgical procedures on extremities that involve irrigation or are associated with fluids.

Figure 2:
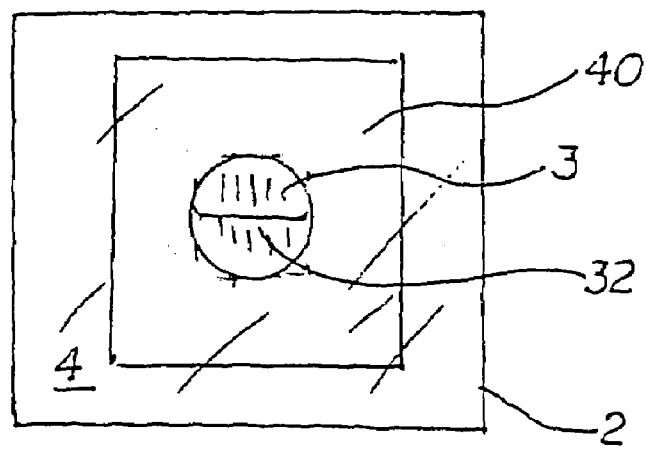
FIG. 2 is a front view of a portion of a drape containing the sleeve in accordance with one embodiment of the invention.

The panel sheet portion 2 comprises a flexible planar body having first and second opposing sides, 4 and 5 respectively, and a fenestration 10 therethrough (see FIGS. 2 and 3) in alignment with the open proximal end 31 of the sleeve portion 3, the proximal end 31 of the sleeve portion 3 being fixed to the region of the panel sheet 2 immediately surrounding the fenestration 10 forming a contiguous drape surface and sterile barrier of material of a combined sleeve 3 and panel sheet 2.

The overall shape or configuration of the panel sheet portion 2 or entire drape 1 can vary in accordance with the procedure or preferences of the user, as well as patient positioning. For example, the shape can be rectangular, square, triangular, circular, T-shaped, and the like. Preferably, the configuration is one which permits "universal" usage, for example, a T-shaped or rectangular drape can be used for either a right or left extremity position. The overall configuration can also be that of the totality of supplemental and integral extension drape attached to the panel sheet portion.

The sleeve portion 3 includes an open proximal end 31 and a closed distal end 32.

Figure 4:
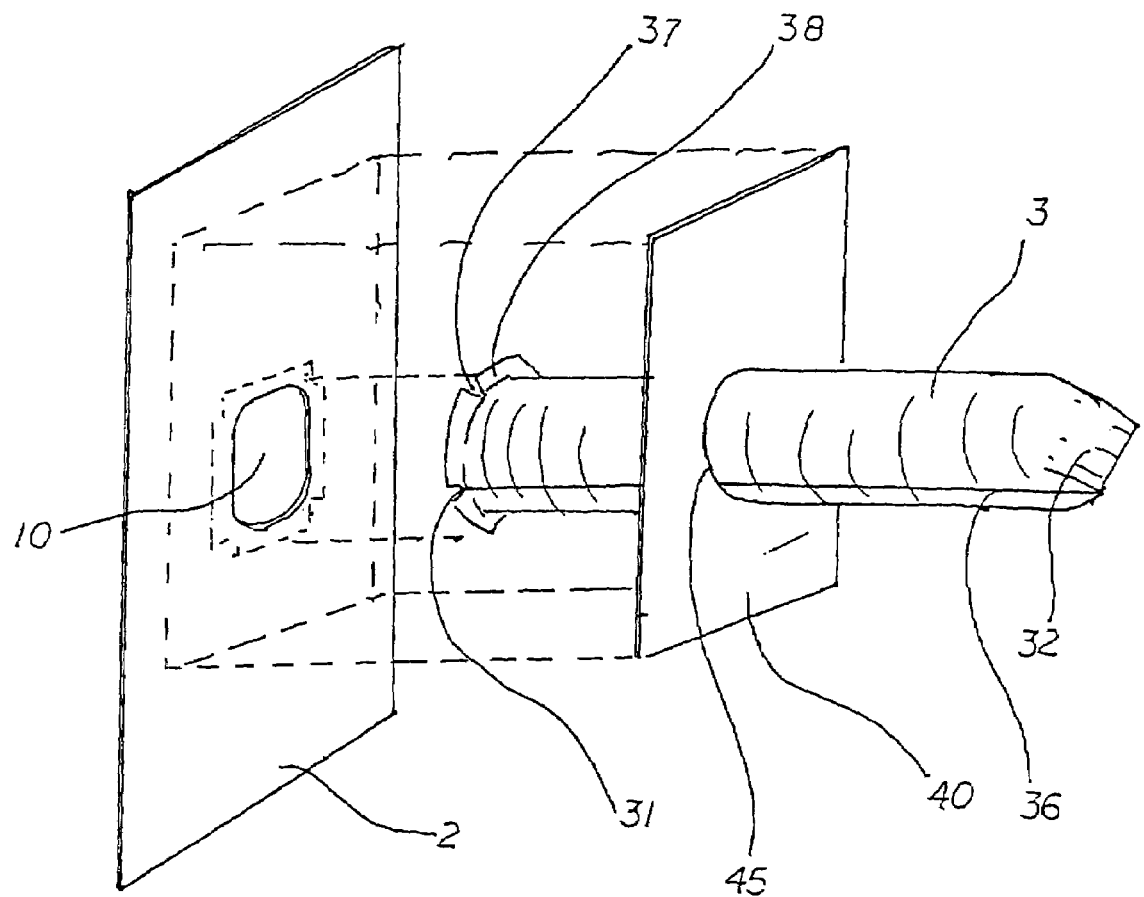
FIG. 4 is a disassembled view showing the components of a portion of a drape in accordance with one embodiment of the invention.
Figure 5:
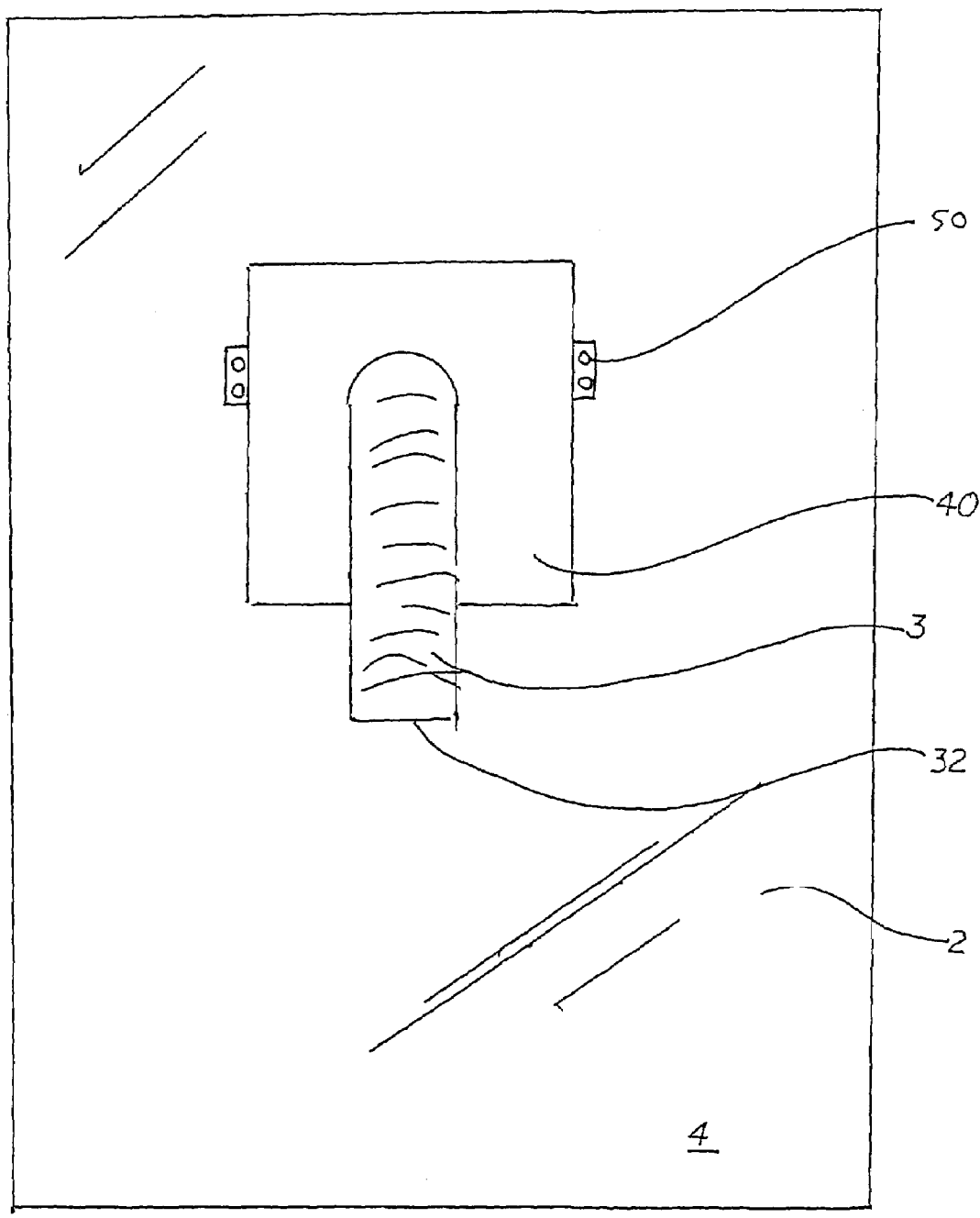
FIG. 5 is a front view of an entire drape according to one embodiment of the invention.

The open proximal end 31 of the sleeve 3 is integrally attached to one side of the panel sheet 2 in a manner circumscribing the region immediately surrounding the fenestration 10 in the panel sheet 2 (see FIGS. 1 and 4).

The sleeve is shown in the figures as having a generally tubular configuration. However, the size, shape and length of the sleeve can vary provided it accommodates the dimensions, e.g., width and length, of the extremity intended to be used therewith. The generally tubular element can include, for example, a uniform cylindrical shape, a tapered configuration, and the like.

The panel sheet portion 2 and sleeve portion 3, as well as a reinforcement panel 40, can be composed of any flexible material suitable for use in a surgical environment and which creates a sterile barrier. The material used for the panel sheet and sleeve can be the same or different material. In a preferred embodiment, the sleeve portion is composed of a fluid impervious material. When fluid impervious material is used for the sleeve portion, the sleeve portion can afford fluid barrier properties and contain fluids generated during a procedure, thereby providing further protection for the user.

A wide variety of flexible materials readily available in the medical field can be used for the panel sheet and/or sleeve portion. Suitable flexible materials include, but are not limited to, woven and non-woven medical fabrics, laminated and intermittently bonded multi-layered materials, plastic and polymeric materials, repellant non-woven materials, absorbent materials, spunlaced, wet laid, reinforced, plastic film, spunbond, and combinations thereof. Non-woven fabrics which can be used, can be prepared by meltblown, spunbonding, bonded carded web processes. Multilaminates that can be used include spunbonded-meltblown-spunbonded (SMS) materials, as well as other layer arrangements, such as SMMS, SM, SFS, and the like. Laminated materials that can be used include those described in Perkins et al. U.S. Pat. No. 5,178,931, Collier et al. U.S. Pat. No. 5,169,706, Brock et al. U.S. Pat. No. 4,041,203, the entire text of which are incorporated herein by reference. Again, it is preferred that the material used for the sleeve portion possess fluid impervious properties. In a further preferred embodiment, both the panel sheet material and sleeve portion material are composed of fluid impervious flexible material.

In one embodiment, the interior surface 33 of the sleeve 3 (see FIG. 3) can further comprise additional material(s) which enhance comfort, reinforce the sleeve portion, and/or facilitate placement of the extremity within the sleeve portion, provided such materials are suitable for a surgical environment. Suitable additional materials include, but knit meshes, soft medical fabrics, and the like. Additional materials need not be completely "laminated" into the interior surface of the sleeve, and can be intermittently bonded or peripherally bonded.

Referring now to FIGS. 1, 2, 4 and 5, in order to enhance the securing of the sleeve portion 3 to the panel sheet 2, the invention preferably comprises a reinforcement panel 40. The reinforcement panel 40 functions to afford fluid control and barrier containment, to resist tearing at the panel sheet-to-sleeve juncture, and fortify surrounding area around fenestration. Extent of area coverage of the reinforcement portion can vary, provided immediate area surrounding panel sheet-to-sleeve juncture is reinforced. The reinforcement panel 40 can be composed of the same materials used for the panel sheet or sleeve.

The size and shape of the fenestration 10 can vary. It is preferred, however, that the dimensions of the fenestration be large enough to be "universal", i.e., readily accommodate the width of the extremity regardless of size. The fenestration can be circular, ovular, square, and the like. Preferably, the fenestration is circular so as to better conform to the sleeve when attached and facilitate manufacture.

To facilitate detachment and removal of the sleeve portion from the remainder of the drape, the invention can further comprise a separable region which is structured to facilitate tearing or detachment. Preferably, the separable region is structured to be fluid impervious so as not to compromise sterility prior to intentional separation of the sleeve from the remainder of the drape. Suitable separation structures are regions of thinner or weakened flexible material, and the like.

Additional components can be used to facilitate securing of the drape of the invention onto the patient or equipment during the procedure. For example, tabs 50 (see FIG. 5, for example), loops, one-sided or double-sided adhesive bands or regions can be attached or integrated as part of the drape of the invention.

In another embodiment, an extension panel can be added and attached to the drape of the invention. Suitable extension panels which can be used include, but are not limited to, anesthesia screens, and the like. As with the remainder of the drape, the extension panel is integrally attached to the drape as with the other portions.

Conventional manufacturing techniques and equipment readily available in the art can be used to prepare a drape according to the invention. The drape of the invention can be made as follows, the interrelationship of the components being illustrated in FIG. 4.

A sheet of material from which the panel sheet 2 of the drape is to be formed is provided, and a fenestration 10 is cut in the desired are within the perimeter of the panel sheet using a die-press machine. A sheet of reinforcement material 40 is provided and similarly cut with a fenestration therethrough at a position which will be in alignment with the panel sheet fenestration 10 and outer peripheral dimensions of the sleeve 3 when the reinforcement panel 40 is assembled in association therewith. The fenestration dimensions will vary in accordance with the requirements of the anticipated procedure(s) and/or anatomical dimensions of the patient.

The sleeve portion 3 can then be prepared cutting out from a flexible material a portion having free ends which are then brought together and fused to form a longitudinal seam 36 along the length of the sleeve 3 forming a hollow interior dimensioned to receive an extremity. Preferably, the seam 36 is a fluid impervious seam. The free ends can be fused together using various techniques readily available in the art, including but not limited to, heat sealing, ultrasonic welding, hot melt adhesives, and the like.

Intermittent slits 37 can be created along the edge of the proximal open end 31 of the sleeve 3 forming circumscribing flaps 38, and the sleeve 3 can then be inverted to position the ends of the seam (if created by the sealing technique) on the inside of the sleeve 3. Adhesive can then be applied to the flaps 38 such that when the sleeve 3 is inverted, the panel-sheet contacting surfaces of the flaps 38 contain the tacky surface. The proximal end 31 of the sleeve 3 and flaps 38 are brought into contact with the area of the panel sheet 2 immediately surrounding the fenestration 10 and adhered thereto, thereby securing the sleeve 3 to the panel sheet 2. At this point, the flaps 38 can be further secured to the panel sheet 2 using one-sided adhesive tape (not shown) or other supplemental securing techniques.

After the sleeve 3 is initially secured onto the panel sheet 3, the reinforcement panel 40 can then be added. The reinforcement panel 40 is positioned such that the distal end 32 of the sleeve is inserted through the fenestration 45 of the reinforcement panel 40 and moved over the sleeve 3 is the proximal direction along the length of the sleeve 3 until a surface of the reinforcement panel 40 contacts the surface 4 of the panel sheet 2. The reinforcement panel 40 can be secured to the panel sheet using a variety of techniques. For example, glue, tape, adhesives, fusion welding, intermittent bonding techniques, and the like can be used.

Another aspect of the invention which facilitates the use of the invention is the folding pattern in which the drape is presented to the user. Generally, the larger panel sheet portion 2 of the drape can be folded in a variety of ways in accordance with the manufacturer or user's reference. Preferably, the sleeve 3 is folded apart from the remainder of the drape in a manner which permits controlled length adjustment while being positioned over the patient's extremity. Folding patterns that can be employed include, but are not limited to, rolling, doubling inward, and accordion-folding.

Figure 3:
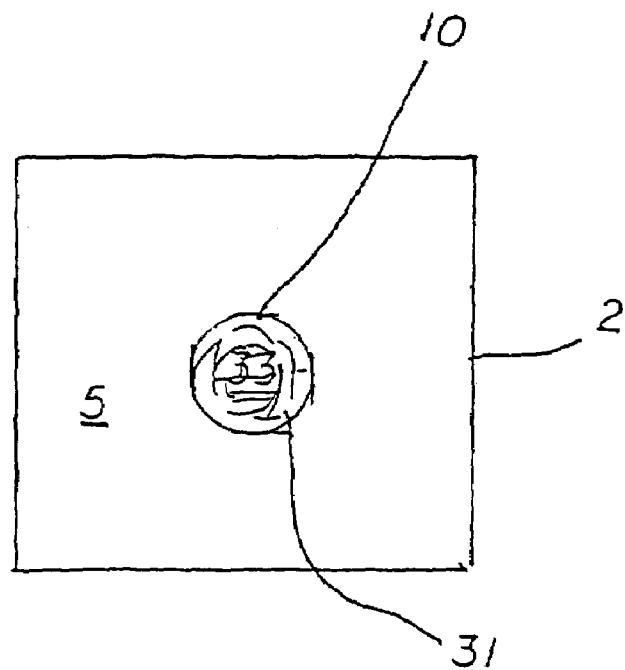
FIG. 3 is a rear view of a portion of a drape exposing the interior of the sleeve in accordance with one embodiment of the invention.
Figures 6A, 6B, 6C, 6D:
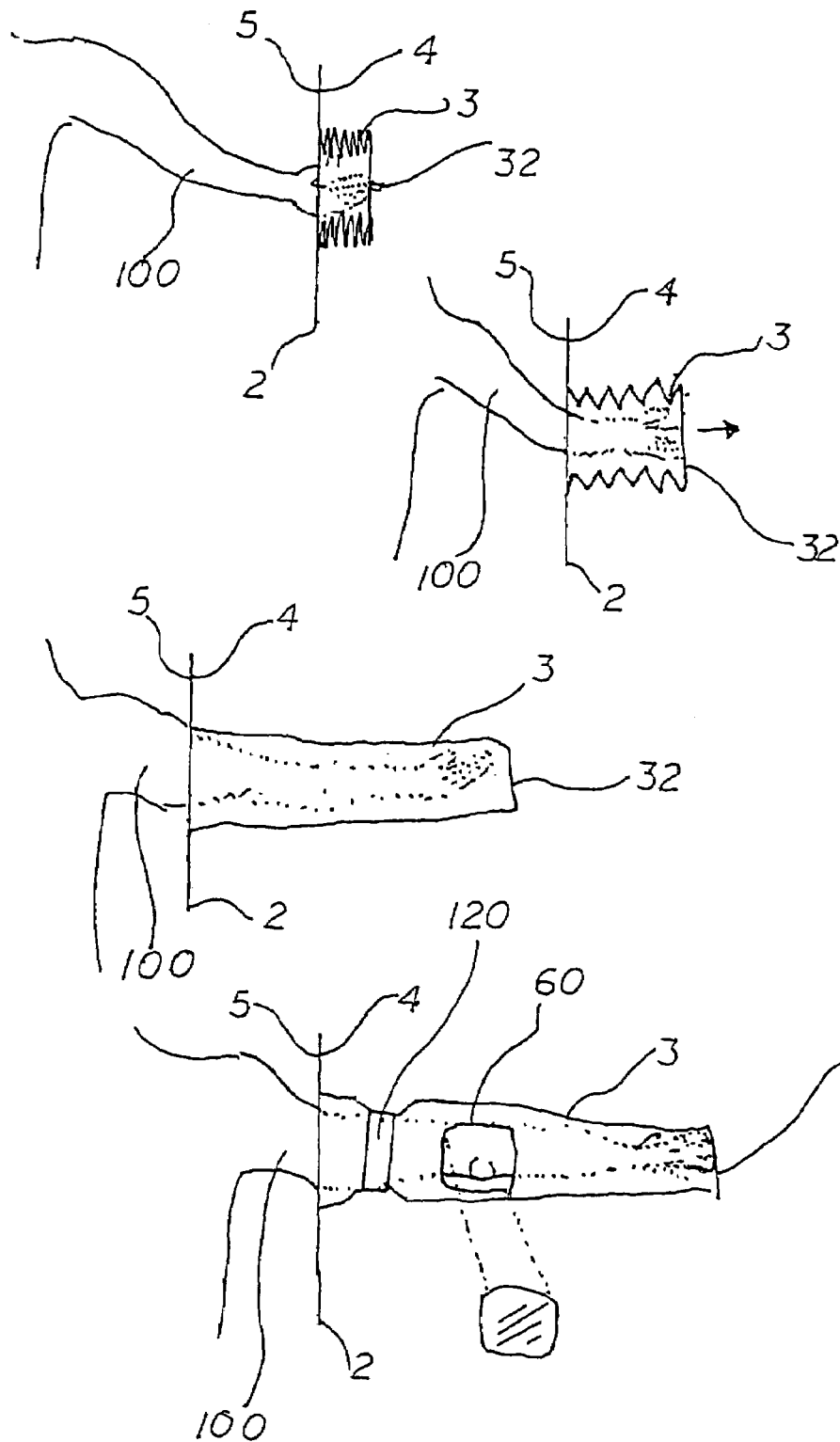
FIGS. 6A through 6D collectively illustrate the use of the drape according to one embodiment of the invention.
Figure 7:
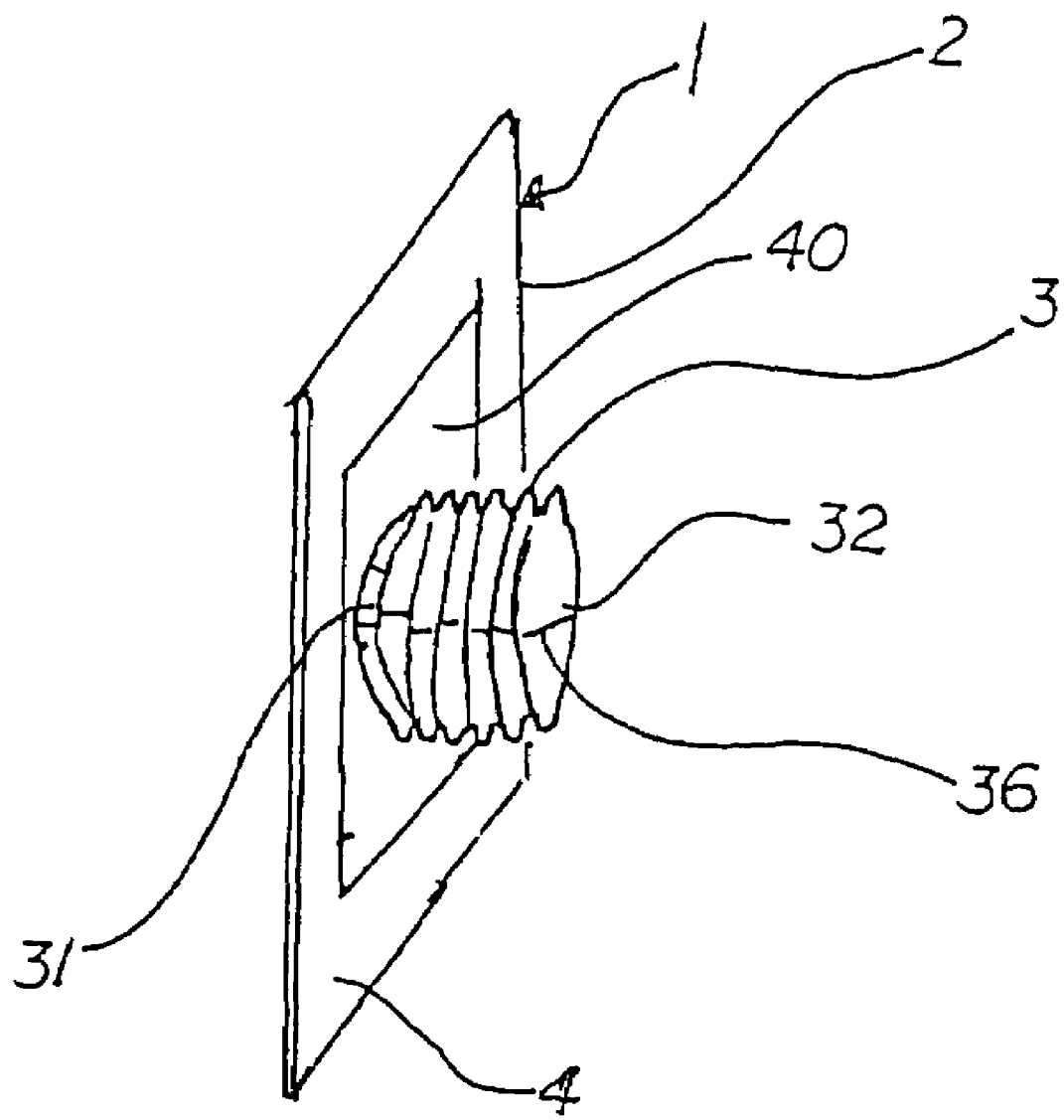
FIG. 7 is a side view of a drape portion showing the sleeve folded in accordance with one embodiment of the invention.

Preferably and as shown in FIG. 7, the sleeve portion is folded in an accordion configuration so as to bring the distal end 32 of the sleeve into 3 proximity with the proximal end 31 of the sleeve 3 and fenestration 10 by folding along the longitudinal axis of the sleeve, and so as to permit viewing of the interior surface 33 of the distal end 32 of the sleeve 3 from the opposite side 5 of the drape through said fenestration 10 (see FIGS. 3 and 7). Accordingly, the interior surface 33 of the distal portion 32 of the sleeve 3, which is where the patient's extremity is initially placed during placement of the drape over the patient (see FIG. 6A), is readily accessible. The accordion-style sleeve folding pattern permits controlled length specific adjustment to the patient's anatomy as shown, for example, in FIGS. 6A, 6B, 6C and 6D, and aids in avoiding compromising sterility by avoiding undesirable non-sterile contact of the interior of the sleeve.

Once the drape of the invention has been positioned onto the patient, a tourniquet structure 120 can be applied circumferentially around the covered extremity to further create a sterile barrier. A variety of suitable tourniquet structures can be used, such as bands, straps, surgical tape, and the like. Subsequently, the practitioner can create a surgical access opening 60 at any location along and around the sleeve to access the extremity (see FIG. 6D). Thus, the drape of the invention does not require a pre-determined access opening. Since the access opening is created at the time of the procedure, the process of choosing one of several pre-designed drapes is eliminated, as is the need for additional drapes to use in conjunction with the extremity drape. Accordingly, the drape of the invention is not only "universal" in that the drape can be constructed to accommodate several anatomical extremities, but also can accommodate numerous surgical locations within a given extremity as well.

In use, the drape is unpackaged and the panel sheet portion can be partially unfolded to expose the fenestration and interior of the sleeve on the patient-contacting side of the drape. Referring now to FIGS. 6A through 6D, the distal end of a patient's extremity 100, such as the hand of an arm, is placed into the interior of the sleeve portion 3 of the drape, and the panel sheet portion 2 is positioned in the desired overall arrangement for the medical procedure. The practitioner can grasp the distal end of the patient's extremity 100 through the outside of the sleeve 3 at the distal end 32 and pull to fully (or partially) extend the sleeve concurrently with the patient's extremity being increasingly covered by the sleeve in the process (see FIG. 6B). Alternatively, though, the patient's extremity itself can be extended into the sleeve from the patient side to expand the sleeve to the appropriate length for the procedure. In either case, it is not always necessary to fully extend the sleeve portion of the drape as shown in FIG. 6C. In this manner, the drape of the invention covers the patient according to patient's individual anatomy and the requirements of the procedure. The sleeve portion or panel sheet portion can be further secured into position in accordance with the preferences associated with the procedure, such as by applying a tourniquet structure 120 (see FIG. 6D). By using the tourniquet structure 120, a further sterile barrier between the sterile, prepped portion of the extremity and the non-sterile, unprepped portion can be created. The practitioner can then create a surgical access opening 60 by cutting an opening through the sleeve material in proximity to the surgical site as illustrated in FIG. 6D.

In a further embodiment of the invention, a fluid collection pouch can be associated with the drape. In one such embodiment, a fluid collection pouch can be presented as an integral component of the drape. Alternatively, a fluid collection pouch can be presented as a separate component to be affixed onto the drape. Fluid collection pouches are well known in the art, and can be constructed with the dimensions and materials according to an intended procedure.

In an alternative embodiment, the distal end of the sleeve portion can be open. In accordance with this embodiment, the step of creating a surgical access opening is not needed. The open-ended sleeve embodiment can be suitable for use on surgical sites located at the distal end of an anatomical extremity. Examples of such surgical sites include, but are not limited to, hands, fingers, feet and toes.

In order to facilitate removal of the drape of the invention after the procedure, the proximal region of the sleeve can further comprise a separation feature 80 structured to facilitate detachment and physical separation of the sleeve portion from the remainder of the drape. A variety of separation features can be used, and can at least partially circumscribe the sleeve. Examples of separation features include, but are not limited to, perforated or thinner portions which can be partially or completely circumscribing the sleeve in the region of the juncture between the sleeve portion and the panel sheet.

INDUSTRIAL APPLICABILITY

The invention is useful to create a sterile barrier in surgical procedures involving anatomical extremities of the patient's body, such as an arm or leg. The drape of the invention is constructed as a convenient single, one-piece drape and reduces or eliminates the need for assembling two or more drapes about the patient. The drape of the invention is also easy and cost effective manufacture, and affords the user ease of use and ease of storage.

The invention has been described herein above with reference to various and specific embodiments and techniques. It will be understood, however, that reasonable variations and modifications can be made to such embodiments and techniques without significantly departing from either the spirit or scope of the invention as defined by the claims set forth below.

What is claimed is:

1. An integrated anatomical extremity drape for use in surgical procedures, the drape comprising:
    a flexible panel sheet having first and second opposing sides and a fenestration therethrough;
    a flexible elongate sleeve sized to accommodate a human limb inserted therethrough, the sleeve having a distal end and a proximal end defining an opening circumscribing the fenestration and being integrally attached to the panel sheet at an attachment juncture; and
    a reinforcement panel having an opening aligned with the fenestration and being attached to the panel sheet surrounding the fenestration so as to reinforce the attachment of the proximal end of the sleeve to the panel sheet at the attachment juncture;
    wherein the sleeve defines an integral separation feature structured to facilitate physical separation of the distal end of the sleeve from the proximal end of the sleeve without disrupting the attachment of the proximal end of the sleeve to the panel sheet at the attachment juncture.

2. The integrated anatomical extremity drape of claim 1, wherein the separation feature is fluid impervious.

3. The integrated anatomical extremity drape of claim 1, wherein the separation feature is defined by a weakened wall of the sleeve.

4. The integrated anatomical extremity drape of claim 1, wherein the separation feature is defined by a thinned wall of the sleeve.

5. The integrated anatomical extremity drape of claim 1, wherein the separation feature at least partially circumscribes the sleeve.

6. The integrated anatomical extremity drape of claim 1, wherein the reinforcement panel covers the attachment juncture.

7. The integrated anatomical extremity drape of claim 6, wherein the reinforcement panel is attached to the first side of the panel sheet corresponding to the elongation of the sleeve so that the opening of the reinforcement panel receives the sleeve.

8. The integrated anatomical extremity drape of claim 7, wherein the proximal end of the sleeve is attached to the first side of the panel sheet corresponding to the elongation of the sleeve such that the sleeve is disposed within the opening of the reinforcement panel but not within the fenestration.

9. The integrated anatomical extremity drape of claim 8, wherein the distal end of the sleeve is closed.

10. The integrated anatomical extremity drape of claim 9, wherein the sleeve is made of a fluid impervious material.

11. The integrated anatomical extremity drape of claim 1, wherein the proximal end of the sleeve has tabs attached to the panel sheet at the attachment juncture.

12. The integrated anatomical extremity drape of claim 1, further comprising an integrated extension panel.

13. The integrated anatomical extremity drape of claim 1, wherein the sleeve is folded in a manner permitting controlled length adjustment.

14. The integrated anatomical extremity drape of claim 13, wherein the sleeve is folded in an accordion configuration so as to bring the distal end of the sleeve into proximity with the proximal end of the sleeve by folding along a longitudinal axis of the sleeve.

15. An integrated anatomical extremity drape for use in surgical procedures, the drape comprising:
    a flexible panel sheet having first and second opposing sides and a fenestration therethrough;
    a flexible elongate sleeve sized to accommodate a human limb inserted therethrough, the sleeve having a distal end and a proximal end defining an opening circumscribing the fenestration and being integrally attached to the panel sheet at an attachment juncture; and
    a reinforcement panel having an opening therein aligned with the fenestration and being attached to the panel sheet surrounding the fenestration so as to reinforce the attachment of the proximal end of the sleeve to the panel sheet at the attachment juncture;
    wherein the sleeve defines an integral fluid impervious separation feature defined by a weakened or thinned wall of the sleeve so as to facilitate physical separation of the distal end of the sleeve from the proximal end of the sleeve without disrupting the attachment of the proximal end of the sleeve to the panel sheet at the attachment juncture.

16. The integrated anatomical extremity drape of claim 15, wherein the separation feature at least partially circumscribes the sleeve.

17. An integrated anatomical extremity drape for use in surgical procedures, the drape comprising:
    a flexible panel sheet having first and second opposing sides and a fenestration therethrough;
    a flexible elongate sleeve sized to accommodate a human limb inserted therethrough, the sleeve having a distal end, a proximal end defining an opening circumscribing the fenestration and an integral separation feature structured to facilitate physical separation the distal end of the sleeve from the proximal end of the sleeve, the proximal end of the sleeve being attached at an attachment juncture to the first side of the panel sheet corresponding to the elongation of the sleeve such that the sleeve is disposed within the opening of the reinforcement panel but not within the fenestration; and a flexible reinforcement panel having an opening therein receiving the sleeve, the reinforcement panel being attached to the first side of the panel sheet corresponding to the elongation of the sleeve and surrounding the fenestration so as to cover the attachment juncture.

18. An integrated anatomical extremity drape for use in surgical procedures, the drape comprising:

a flexible panel sheet having first and second opposing sides and a fenestration therethrough;

a flexible elongate sleeve sized to accommodate a human limb inserted therethrough, the sleeve having a distal end and a proximal end defining an opening circumscribing the fenestration and being integrally attached to the panel sheet at an attachment juncture; and a reinforcement panel having an opening aligned with the fenestration and being attached to the panel sheet surrounding the fenestration so as to reinforce the attachment of the proximal end of the sleeve to the panel sheet at the attachment juncture;

wherein the sleeve defines an integral separation feature at the region of juncture between the sleeve and the panel sheet structured to facilitate physical separation of at least a portion of the sleeve from the remainder of the drape.

* * * * *